United States Patent [19]
Van Der Greef et al.

[11] Patent Number: 6,080,590
[45] Date of Patent: *Jun. 27, 2000

[54] ON-LINE COUPLING BIOCHEMICAL DETECTION TO CONTINUOUS FLOW SEPARATION TECHNIQUES

[75] Inventors: Jan Van Der Greef, Austerlitz; Hubertus Irth, Amsterdam; Aaike Johannes Oosterkamp; Eva Saskia Mareike Lutz, both of Leiden, all of Netherlands

[73] Assignee: Rijksuniversiteit te Leiden, Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/632,540

[22] Filed: Apr. 19, 1996

Related U.S. Application Data

[63] Continuation-in-part of application No. 08/427,085, Apr. 21, 1995, abandoned.

[51] Int. Cl.[7] ..................... G01N 33/536; G01N 33/537; G01N 33/53; C12Q 1/70
[52] U.S. Cl. .............................. 436/536; 436/538; 435/5; 435/7.1; 435/7.2; 435/7.9; 435/DIG. 1; 435/DIG. 2; 435/DIG. 9; 435/DIG. 14; 435/DIG. 16; 435/DIG. 17; 435/DIG. 18; 435/DIG. 22; 210/656
[58] Field of Search ..................................... 436/536, 538; 435/5, 7.1, 7.2, DIG. 1, DIG. 2, DIG. 9, DIG. 14, DIG. 16, DIG. 17, DIG. 18, DIG. 22, 79; 210/656, 198.2

[56] References Cited

U.S. PATENT DOCUMENTS 3,912,589  10/1975  Smith, et al. ............................. 195/29
4,401,567  8/1983   Shindo et al. ........................... 210/500
5,277,821  1/1994   Coughlin et al. ....................... 210/644

OTHER PUBLICATIONS

R.J. Miksicek: Interaction of naturally occuring nonesteroidal estrogens . . . : J. Steroid Biochem. Mol. Biol.: V. 49 (2–3): Abstract, 1994.

Irth, et al.: On–line immunochemical detection in liquid chroatography . . . : J Chrom. :633: pp 65–72, 1993.

Harlow, et al. Antibodies–a laboratory manual: pp. 555–583, 1988.

*Primary Examiner*—Jeffrey Stucker
*Assistant Examiner*—Breh Nelson
*Attorney, Agent, or Firm*—Michaelson & Wallace; Peter L. Michaelson

[57] ABSTRACT

The present invention relates to an on-line detection method comprising the on-line coupling of a fractionation and a biochemical detection technique, which method comprises the addition of a controlled amount of an affinity molecule to the effluent of the fractionation step to react with analytes in the effluent, the subsequent addition of a controlled amount of a detectable ligand capable of binding to the affinity molecule, and detection of the affinity molecule/ detectable ligand complex. Further, the invention is directed to an on-line method for the screening of compounds on their binding capability to a known affinity molecule, which method comprises a fractionation step providing an effluent, the addition of a controlled amount of said affinity molecule to the effluent of the fractionation step and effecting a contact time sufficient to allow a reaction with or interaction between the compounds in the effluent, the subsequent addition of a controlled amount of a detectable ligand capable of binding to the affinity molecule, and detection of the affinity molecule/detectable ligand complex.

14 Claims, No Drawings

ON-LINE COUPLING BIOCHEMICAL DETECTION TO CONTINUOUS FLOW SEPARATION TECHNIQUES

This application is a continuation-in-part application of U.S. patent application Ser. No. 08/427,085 filed on Apr. 21, 1995, now abandoned, and entitled "On-Line Coupling of Biochemical Detection to Continuous-Flow Separation Techniques".

The present invention relates to the on-line coupling of biochemical detection to continuous-flow separation techniques. In a further embodiment, this on-line detection method is used as a screening method.

It is well-known to the person skilled in the art that immunoassays are highly sensitive detection techniques which combine the selectivity of biospecific interactions with the sensitive detection of labels used as reporter molecules.

An example of such a technique is described in WO 91/13354. This document describes a flow immunosensor wherein an antibody specific to a target is immobilized an a support. The antibody's binding sites are saturated with a labelled form of the target. A liquid to be analyzed is flown past the antibody to allow any target present in the liquid to displace the labelled antigen. Finally, the displaced labelled antigen is detected.

However, it is known as well that immunoassays suffer from the problem of cross-reactivity, which means that antibodies react with more than one analyte. This leads to erroneous results. For this reason, immunoassays are frequently combined with a fractionation step, e.g., a separation step using HPLC or another type of liquid chromatography.

In the field to which the present invention relates, there is a want for on-line coupling of a fractionation step and an immunoassay detection system. Several approaches have been proposed and described to perform continuous-flow immunoassays. Most of these immunoassays are in the form of a postcolumn reaction detection system based on a sequential addition type immunoassay.

Cassidy et al., Anal. Chem. 64 (1992), 1973–1977 disclose a kinetically controlled immunoassay based on the sequential addition of antibody, sample and label on a protein A column, performing immunoassays for albumin and transferrin in less than 1 minute.

Nilson et al., J. Chromatography, 597 (1992) 383–389 describe a continuous-flow competitive assay involving enzyme-labelled antibodies. The system described was coupled to a size-exclusion column to allow the monitoring of activity.

These prior art techniques which are of a sequential nature are not suitable for on-line coupling to liquid chromatographic or other fractionation systems, since these techniques do not allow the continuous monitoring of the fractionation effluent.

In the article of Irth et al. in the Journal of Chromatography 633 (1993) 65–72 and in the articles of Oosterkamp et al. in Anal. Chem. 66 (1994) 4295–4301, and in the Journal of Chromatography 653 (1994) 55–61, a method for the on-line detection of digoxin and its metabolites is described. The on-line detection process comprises the direct injection of a sample containing digoxin and its metabolites, a liquid chromatographic (LC) fractional separation step, the mixing of the effluent of the LC column with fluorescein-labelled antibodies against digoxigenin, the removal of free labelled antibodies from the mixture via passage through a small column packed with an antigen-bound support, and detection of the strongly fluorescent immunocomplexes.

The digoxigenin system described is based on association reactions of antibodies and antigens eluting from the analytical column. By the use of fluorescein-labelled antibodies detection limits in the nanomolar range are obtained.

This prior art assay is a heterogeneous detection system. It requires a separation step between free and bound label. Examples for free/bound label separation techniques are restricted-access phases and hollow-fibre modules.

The immunoreagent in the previously described prior art assay consists of fluorescein-labelled fragments of anti-digoxigenin antibodies which were immunopurified and are commercially available. The commercial availability of purified, labelled antibodies is however exceptional. In almost all cases, antibodies are only available in unlabelled state in crudely purified antiserum. Although labelling and purification schemes for antibodies (or other affinity proteins) are known to the person skilled in the art, it will be preferred to use antisera, which may be commercially available, without any pretreatment.

Furthermore, it is difficult to selectively label only those antibodies in an antibody preparation which are reacting with the analytes. In general, labelling techniques make use of primary amine groups of antibodies resulting in the colabelling of all other proteins present in the preparation. This leads to a drastic increase in the background signal and, consequently, to an increase in detection limits.

The aim of the invention is to provide alternatives for this known technique, which technique makes use of fluorescein-labelled antibodies. The embodiments of the present invention do not have the disadvantages associated with the labelling of antibodies.

In more detail, the problem underlying the present invention is the provision of an on-line detection technique without requiring the use of labelled antibodies.

This problem is overcome by the provision of an on-line detection method comprising the on-line coupling of a fractionation step and a biochemical detection technique, which method comprises the addition of a controlled amount of an affinity molecule, such as an affinity protein or a receptor, to the effluent of the fractionation step which affinity molecules bind with analytes in the effluent, the subsequent addition of a controlled amount of a detectable ligand, such as a labelled ligand, capable of binding to the affinity molecule, and detection of the affinity molecule/detectable ligand complex.

The reduction in the amount of detected affinity molecule/detectable ligand complex indicates the presence of an affinity molecule-binding compound in the effluent.

In particular, in a first step, a suitable affinity molecule for analytes to be detected—which affinity molecule may e.g. be an affinity protein, such as an antibody or avidin—is added to the effluent of a liquid chromatography or a capillary electrophoresis column to react with ligands or analytes eluting from the column. Unbound affinity molecules react in a second step with an excess of a detectable ligand, which may be the analyte to be detected in labelled form, such as a fluorescein-labelled analyte to titrate the remaining free binding sites; or as an alternative, a competition reaction occurs between the affinity molecule, the analyte in the effluent and the detectable ligand. Normally, the labelled ligand/affinity molecule complex is detected after a separation of free and bound labelled ligand, preferably on the basis of the difference in molecular weight. Finally, the labelled ligand/affinity molecule complex is detected.

The combination of the fractionation step with the biochemical detection step in accordance with the present invention greatly enhances the performance of both techniques. The combined techniques provide an analytical method which is characterized by a high selectivity and a high sensitivity. Further, the problem associated with cross-reactivity no longer occurs when using the method of the present invention.

The method of the present invention uses bioaffinity molecules such as antibodies, receptors etc. to detect any compounds showing high affinity for the ligand binding site of said affinity molecule. The compounds to be detected may be biochemical compounds but are not in any way restricted thereto.

The method of the invention makes it possible to screen a mixture of different compounds on their ability to bind to a certain affinity molecule, e.g., in order to find an inhibitor for said affinity molecule. Therefore, the present invention further relates to a fast on-line method for the screening of compounds for their binding capability to a known affinity molecule. The invention method involves a fractionation step which yields an effluent to which is added a controlled amount of the affinity molecule. Contact is continued for a time period sufficient to permit reaction with or interaction with the components of the effluent. Following, a controlled amount of detectable ligand capable of bonding to an affinity molecule is added and detection of the affinity molecule/ detectable ligand complex occurs. The reduction in the amount of detected affinity molecule/detectable ligand complex indicates the presence of an affinity molecule-binding compound in the effluent.

A comparison of the detection signal obtained when analytes are injected with the signal obtained when only the controlled amounts of affinity molecule and detectable ligand are introduced in the continuous-flow system, provides information in respect of the percentage of the binding sites occupied by analytes present in the effluent of the fractionation step. The person skilled in the art possesses the knowledge to process and evaluate the data obtained from the detection method. The percentage binding sites occupied by an analyte present in the effluent can be used to find new compounds which show an interaction with a known affinity molecule. This information provides the possibility to implement the on-line separation/affinity molecule detection process of the present invention in, drug discovery.

A system of high-throughput screening to be used in drug discovery may, for instance, consist of the following steps. Complex samples generated, by an upstream combinational chemistry system are prefractionated in fractions containing compounds of similar polarity using, a solid-phase extraction technique or electrophoretic sample handling principles. Each fraction may additionally be separated using, e.g., either analytical or preparative-scale liquid chromatographic separation columns. The compounds eluting from said LC column are on-line detected using a suitable affinity molecule detection technique. Where preparative-scale separation columns are applied, a post-column flow-split will be made. One of the two flow streams is subjected to detection using the affinity molecule detection technique; the other stream is directed to a fraction collector. Dependent on the signal obtained from the affinity molecule detector, fractions containing compounds causing a positive response will be collected while fractions causing a negative response will be discarded. This complete screening method can be automated using known valve-switching processes.

A suitable fractionation method to be used in the methods of the present invention comprises a liquid chromatography separation or a capillary electrophoresis step. Other separation or fractionation techniques which are known to the person skilled in the art and which allow a relatively continuous output stream can, however, be used as well.

In a preferred embodiment, the liquid chromatography separation step is a reversed phase HPLC step.

In a very advantageous embodiment the separation of free and bound label is performed on the basis of molecular weight using selective membrane modules. Preferably hollow-fibre membrane modules are used. The reaction mixture containing free and bound label passes along the selective membrane or is pumped through the inner capillary of a hollow-fibre membrane. Using well-known membrane separation techniques such as ultra filtration, liquid is forced through the membrane and is collected at the acceptor or permeate side. The collected liquid is subsequently directed to a suitable label detector system, e.g. a fluorescence detector. The molecular weight cut-off of the membrane can be chosen so as to allow that only relatively low molecular weight compounds, such as free label, can reach the acceptor side. High molecular weight compounds remain in the mother reaction mixture. By using the selective membrane separation technique, principally all kinds of affinity proteins can be used, inclusive of all membranes or cell membrane fragments. It is not necessary that the affinity proteins be completely soluble or solubilized. Cell suspensions can be handled by means of the selective membrane modules and in particular the hollow-fibre modules.

The detection method which forms an integral part of the methods of the present invention can be chosen dependent on a suitable detectable ligand. Examples of suitable detection methods comprise methods based on all types of luminescence detection principles, such as fluorescence, time-delayed fluorescence and chemiluminescence spectroscopy; methods based on electrochemical detection and on radiometric detection.

In the methods of the present invention all molecules capable of interaction with or binding to other molecules can be used as affinity molecule. In preferred embodiments, the affinity molecule is selected from the group of cytosolic receptors, e.g., the estrogen, glucocorticoid receptors; solubilized membrane bound receptor, e.g., a β-receptor; affinity proteins, such as antibodies, enzymes, avidin; polynucleotides and polysaccharides.

Furthermore, the affinity molecule may be an "orphan" receptor. Such molecules are thought to be nuclear receptors, as they are structurally related to characterized receptors, but for which no ligand has been identified. The determination of ligands for orphan receptors is relatively slow. By using the method of the present invention, this determination can be accelerated.

The term "detectable ligand" as used in the present description and claims refers to a ligand which is capable of interacting or reacting with the afore-defined affinity molecule, and which can be detected in a biochemical detection method. An example of a detectable ligand is a labelled analyte.

If labelled antigens are used instead of the labelled antibodies used in the prior art techniques described above, two major advantages are obtained. First, it is easier to prepare and, particularly, purify low-molecular weight labelled antigens. Second, the background noise signal problem obtained in the preparation step of labelled antibodies does not occur when labelled antigens are used for immunodetection.

As to the above-described selective membrane separation embodiment, the two following advantages in respect of suitable labels can be mentioned. This separation technique is independent from the physico-chemical properties of the label, and in particular the polarity thereof. Unlike in restricted access solid support separation systems, highly polar labels can be used. By choosing the proper membrane cut-off, enzymes can be used as labels, as well. This gives the possibility to use enzyme-labels which are originally prepared for e.g. ELISA systems. The skilled person will realize that this possibility extends the range of applications.

On-line coupling as used in the methods of the present invention requires fast reaction times in order to minimize extra-column band broadening. This means that affinity molecule-ligand interactions having reaction times in the order of minutes rather than hours should be considered.

In one embodiment of the method of the invention, biotinylated DNA-fragments are determined by the continuous addition of avidin to the eluate of a HPLC column. The avidin is allowed to react with the biotinylated DNA-fragments in a so-called reaction coil. Subsequently, a continuous flow of a solution comprising fluorescein-labelled biotin is added in the flow leaving the reaction coil. In a following step in the continuous flow process, free and avidin-bound fluorescein-labelled biotin are separated from each other, e.g., by the use of a separation procedure making use of the difference in molecular weight between free and bound biotin, such as running the free and avidin-bound fluorescein-labeled biotin sample on a column packed with $C_{18}$-silica restricted access support. The high-molecular weight labelled ligand/protein complex passes the $C_{18}$-column unretained and is subsequently detected by means of fluorescence detection. For the biotin-avidin system a detection limit in the order of 100–500 fmol was obtained for biotin.

The methods of the present invention can be applied as well to systems wherein a DNA or RNA probe is used as a receptor for DNA and/or RNA derived analytes. In this case, the detectable ligand may be a (part of the) complementary strand which can, e.g., labelled with a radioactive isotope.

In a very advantageous embodiment within the scope of the present invention no separation step between free and bound label is needed. Techniques wherein the separation step is omitted are called homogeneous techniques. Such techniques can be used in accordance with the method of the present invention in all cases wherein free and receptor-bound labels differ significantly in a detection signal, e.g. in fluorescence intensity, excitation or emission wavelength, enzyme activity and so on.

An example of such a homogeneous embodiment is an embodiment wherein the affinity molecule used is the estrogen receptor and the detectable ligand is coumestrol or another natively fluorescent estrogenic ligand. In this embodiment it is also possible to use the steroid binding domain of the human estrogen receptor, which can, e.g., be prepared by gene technology, instead of the complete estrogen receptor. This embodiment does not require a separation step wherein bound and free coumestrol are separated. Coumestrol is a compound which provides a strong fluorescent signal when bound to the estrogen receptor, and provides a weak fluorescent signal in free state. Since coumestrol and the estrogen receptor are introduced in the continuous-flow system of the present invention in controlled amounts, a comparison of the fluorescence signals obtained will give information as to how many binding sites of the estrogen receptor are occupied by coumestrol and how many binding sites are occupied by competitive analytes. Although this embodiment using the steroid binding domain of the estrogen receptor and coumestrol or another natively fluorescent estrogenic ligand does not require a separation step wherein bound and free coumestrol are separated, the fluorescence data will provide more detailed qualitative and quantitative information if such a separation step is carried out.

The present invention will be described in further detail while referring to the following examples.

EXAMPLE 1

Biotin was applied to a liquid chromatography (LC) column. The LC separation was carried out on a 100×3.0 mm i.d. stainless-steel column packed with Nucleosil $C_{18}$ (5 μm particles, Macherey-Nagel, Düren, Germany) using methanol/aqueous triethylammonium acetate (10 mmol/l; pH 7.0) 10:90 (v/v) as a mobile phase, which mobile phase was delivered by means of a Kratos-ABI (Ramsey, U.S.A.) Spectroflow 400 pump. In the effluent of the LC separation step, avidin was delivered in binding buffer consisting of sodium phosphate (10 mmol/l, pH 8.0; Merck, Darmstadt, Germany) containing 0.5 mol/l sodium chloride (analytical grade; Merck, Darmstadt, Germany), the avidin concentration being 34 nmol/l, by means of a Pharmacia (Uppsala, Sweden) P3500 pump (flow rate 0.4 ml/min). The combined avidin-biotin flow was introduced in a knitted 0.5 mm internal diameter (i.d.) poly(tetrafluoroethylene) reaction coil with an internal volume of 800 μl. Subsequently, fluorescein-labelled biotin (Sigma, St. Louis, U.S.A.) was delivered in the mobile phase at a flow rate of 0.8 ml/min using a Kratos-ABI Spectroflow 400 pump. The flow obtained was introduced in a knitted 0.5 mm i.d. poly (tetrafluoroethylene) reaction coil with an internal volume of 400 μl. The reactions were performed at 20° C.

Separation of free and avidin-bound fluorescein-biotin was performed using a 10×4.0 mm i.d. column packed with $C_{18}$ alkanediol silica (described in DE-A-41 30 475). After this column, the flow was introduced in a fluorescence detector (Merck 1080 fluorescence detector; excitation wavelength 486 nm; emission wavelength 520 nm).

The absolute detection limit obtained for biotin was 160 fmol. The detection system provided a linear signal ranging from 8 to 200 nmol/l (20 μl injections).

EXAMPLE 2

A mixture consisting of $T_6$-biotin (0.5 μM) and $T_3$-biotin-$T_3$ (0.5 μl) representing biotinylated DNA-fragments was injected onto an LC column. The LC separation was carried out on a 100×3.0 mm i.d. stainless steel column packed with Nucleosil $C_8$ (5 μm particles, Macherey-Nagel, Düren, Germany) using acetonitrile/aqueous triethylammonium acetate (10 mM, pH 7.0) 7:93 (v/v) as a mobile phase, which mobile phase was delivered by means of a Kratos-ABI (Ramsey, U.S.A.) Spectroflow 400 pump. In the effluent of the LC separation step, avidin was delivered in binding buffer consisting of sodium phosphate (10 mmol/l, pH 8.0; Merck, Darmstadt, Germany) containing 0.5 mol/l sodium chloride (analytical grade; Merck, Darmstadt, Germany), the avidin concentration being 34 nmol/l, by means of a Pharmacia (Uppsala, Sweden) P3500 pump (flow rate 0.4 ml/min). The combined avidin-biotinylated compounds flow was introduced in a knitted 0.5 mm i.d. poly (tetrafluoroethylene) reaction coil with an internal volume of 800 μl. Subsequently, fluorescein-labelled biotin (Sigma, St. Louis, U.S.A.) was delivered in the mobile phase at a flow rate of 0.8 ml/min using a Kratos-ABI Spectroflow 400 pump. The flow obtained was introduced in a knitted 0.5 mm i.d. poly(tetrafluoroethylene) reaction coil with an internal volume of 400 μl. The reactions were performed at 20° C.

Separation of free and avidin-bound fluorescein-biotin was performed using a 10×4.0 mm i.d. column packed with $C_{18}$ alkanediol silica (described in DE-A-41 30 475). After passing this column, the flow was introduced in a fluorescence detector (Merck 1080 fluorescence detector; excitation wavelength 486 nm; emission wavelength 520 nm).

It appeared that the retention times of $T_3$-biotin-$T_3$ and $T_6$-biotin were 6.2 and 6.6 minutes, respectively.

EXAMPLE 3

A mixture of compounds which bind to steroid receptors, 17β-estradiol, estriol, diethylstilbestrol, zeranol, estrone, progestrone, testosterone and dexamethasone (concentration: 100 nmol/l; injection 20 μl) was applied to a LC column. The LC separation was carried out on a stainless-steel column packed with Nucleosil $C_2$ (5 μm particles, Macherey-Nagel, Düren, Germany) using acetonitrile:methanol: potassium phosphate buffer (10 mM, pH 7.4) 20:20:60 (v/v) as a mobile phase, which mobile phase was delivered by means of a Kratos-ABI (Ramsey, U.S.A.) Spectroflow 400 pump at a flow rate of 0.5 ml/min. In the effluent of the LC separation step, estrogen receptor (human estrogen receptor steroid binding domain; Karo-Bio, Huddinge, Sweden) was delivered in a potassium phosphate buffer (200 mmol/l, pH 7.4; Merck, Darmstadt, Germany), the estrogen receptor concentration being 5 nmol/l, by means of a Pharmacia (Uppsala, Sweden) P3500 pump (flow rate 0.5 ml/min). The combined estrogen-analytes flow was introduced in a knitted 0.5 mm i.d. poly(tetrafluoroethylene) reaction coil with an internal volume of 900 μl. Subsequently, coumestrol (Eastman-Kodak, Rochester, New York, U.S.A.) in a concentration of 111 nmol/l in the potassium phosphate buffer was delivered in the mobile phase at a flow rate of 0.5 ml/min using a Kratos-ABI Spectroflow 400 pump. The flow obtained was introduced in a knitted 0.5 mm i.d. poly(tetrafluoroethylene) reaction coil with an internal volume of 570 μl. The reactions were performed at 20° C.

Subsequently, the flow was introduced in a fluorescence detector (Merck 1080 fluorescence detector; excitation wavelength 340 nm; emission wavelength 410 nm). It was found that 17β-estradiol, estriol, diethylstilbestrol, zeranol and estrone could be detected in a concentration of 50 nmol/l, whereas progestrone, testosterone and dexamethasone did not provide any response at concentrations of 100 nmol/l.

EXAMPLE 4

In this example use is made of a flow injection (FI) system consisting of three HPLC pumps, viz. one Jasco 88 PU and two Spectroflow 400-ABI Analytical Kratos Division pumps, a six-port injection valve (Rheodine, Berkley, USA) with an injection volume of 20 μl, a Merck-Hitachi F-1080 Fluorescence detector (time constant 8 seconds; excitation wavelength 486 nm and emission wavelength 516 nm), and a Kipp & Zonen BC 40 recorder. Phosphate buffered saline (PBS; pH 8.0) containing 0.5 wt. % Tween 20 was used as carrier solution. The flow rate was 0.2 ml/min. Solutions of 6.67 nM; immunopure goat anti-biotin (Pierce, 31852X); 13.33 nM binding sites) and of 13.33 nM fluorescein-biotin (5-biotinamidocaproylamido)pentylthioureidyl fluorescein, Sigma, B8889, lot 8 H0077) were prepared in PBS containing 0.5 wt. % Tween 20. These solutions were added to the FI carrier containing D(+) biotin (Merck, Germany) via a t-type and a y-type mixing union with a flow rate of 0.2 ml/min. After the addition of the antibody solution, the flow passed a knitted 0.5 i.d. PTFE reaction coil with an internal volume of 142 μl; after the addition of labelled antigen solution, the flow passed a knitted 0.5 e.d. PTFE reaction coil with an internal volume of 167 μl. The system was run at room temperature.

The reaction mixture flow obtained comprising free and antibody-bound antigen was directed to a hollow-fibre module consisting of one capillary cross flow membrane type UFM, M5 of 12 cm length, i.d. 1.5 mm, molecular weight cut-off 100 kD (X-Flow B.V., Almelo, the Netherlands). The module was manufactured from Plexiglas with a circular channel of 3.0 mn i.d. and screw inlets at both ends as well as at the side of both ends. The PTFE-tubing was inserted into the hollow fibre; 2 mm of silicon-tubing was put around both the hollow fibre and the tubing, an O-ring and a fingertight with a flat end were put on the tubing and screwed into the Plexiglas. The silicon tubing serves as ferule, tightening both the hollow fibre and the PTFE-tubing. The O-rings prevent frictional forces upon tightening the hollow fibre. The side connection at the inlet of the module was closed with a knotted silicon tube, the outlet was connected to a Gilson restrictor, forcing all the fluid through the membrane to the side connection at the outlet, which leads to the fluorescence detector.

A concentration dependent signal was obtained. Free fluorescein-biotin was separated from the antibody-bound labelled antigen by means of the capillary cross-flow membrane. Responses were obtained in the range of 1 μg/l to 10 mg/l (4 nM–40 μm) using different biotin concentrations.

EXAMPLE 5

Example 4 was repeated, except for the horseradish peroxidase (HRP) labelled biotin (Sigma) at a concentration of 7.4 nM in PBS (=0.5 wt. % Tween 20) and a substrate solution of 83.3 μm 3-p-hydroxyphenylpropionic acid (HPPA) and 20 mM $H_2O_2$ were used, instead of the fluorescently labelled antigen. The substrate solution was added at the inlet side of the hollow-fibre module using a Gilson Model 302 HPLC pump. Biotin was allowed to react first with the antibodies and then with the HRP labelled antigen using reaction coils of 900 and 570 μl were used, respectively.

Separation of free and antibody-bound labelled antigen occurred: the HRP-biotin of ±45 kD is able to pass the membrane freely, whereas the antibody-bound fraction of ±195 kD is retained. The substrate solution was added to the acceptor flow, creating a fluorescent signal. In comparison to an immunochemical detection system using fluorescein-biotin, this set-up leads to at least similar responses.

The timeframe for these detection set-ups is about 7 min, consisting of 3 min of reaction time and 3.5 min for the peak to be finished.

What is claimed is:

1. An on-line continuous method for analyzing analytes in the effluent of a fractionation step which comprises the steps of (a) continuously adding a controlled amount of an affinity molecule capable of binding with the analytes of said effluent, thereby forming a first mixture, (b) continuously introducing said first mixture into a first means for a defined residence time, thereby permitting binding of said affinity molecule with analytes present in the effluent, (c) continuously adding a controlled amount of a detectable ligand to the product of step (b), at least a portion of said ligand being capable of binding with remaining affinity molecule, so forming a second mixture, (d) continuously introducing said second mixture into a second means for a defined residence time, so resulting in the formation of an affinity molecule-detectable ligand complex and unbound detectable ligand, (e) continuously introducing the effluent of step (d) into a restricted access module wherein the unbound detectable ligand is retained and the affinity molecule-detectable ligand complex forms a continuous effluent, and (f) detecting the amount of complex in said continuous effluent.

2. Method in accordance with claim 1 wherein the fractionation step is effected by liquid chromatography or electrophoresis.

3. Method in accordance with claim 2 wherein the fractionation step is effected by liquid chromatography by HPLC or reversed phase HPLC.

4. Method in accordance with claim 1 wherein detection is effected by fluorescence, time delayed fluorescence and chemiluminescence spectroscopy or electrochemical or radiometric detection.

5. Method in accordance with claim 1 wherein the affinity molecule is selected from the group consisting of a nuclear receptor, an intracellular receptor, a solubilized receptor, an antibody, an enzyme, avidin, a polynucleotide and a polysaccharide.

6. Method in accordance with claim 1 wherein the detectable ligand is a labelled ligand.

7. Method in accordance with claim 1 wherein the affinity molecule is an estrogen receptor or a portion thereof.

8. Method in accordance with claim 7 wherein the affinity molecule is an estrogen receptor or the steroid binding domain thereof and the detectable ligand is coumestrol.

9. Method in accordance with claim 1 wherein the method is effected downstream of a combinatorial chemistry system including a fractionation step which provides the effluent.

10. Method in accordance with claim 1 wherein the affinity molecule is an orphan receptor.

11. Method in accordance with claim 1 wherein the detectable ligand has a fluorescence signal which differs from the fluorescence signal of the affinity molecule-detectable ligand complex and detection thereof is effected by means of the differing fluorescence signal.

12. Method in accordance with claim 1 wherein said first and said second means comprises a reaction coil.

13. An on-line continuous method for analyzing analytes in the effluent of a fractionation step which comprises the steps of (a) continuously adding a controlled amount of an affinity molecule capable of binding with the analytes of said effluent, thereby forming a first mixture, (b) continuously introducing said first mixture into a first means for a defined residence time, thereby permitting binding of said affinity molecule with analytes present in the effluent, (c) continuously adding a controlled amount of a detectable ligand to the product of step (b), at least a portion of said ligand being capable of binding with remaining affinity molecule, so forming a second mixture, (d) continuously introducing said second mixture into a second means for a defined residence time, so resulting in the formation of an affinity molecule-detectable ligand complex and unbound detectable ligand, (e) continuously introducing the effluent of step (d) into a hollow fibre module wherein the affinity molecule-detectable ligand complex is retained and the unbound detectable ligand forms a continuous effluent, and (f) detecting the amount of complex in said continuous effluent.

14. Method in accordance with claim 13 wherein said first and said second means comprises a reaction coil.

* * * * *